(12) United States Patent
Rana et al.

(10) Patent No.: US 10,383,806 B2
(45) Date of Patent: Aug. 20, 2019

(54) COMPOSITIONS INCLUDING SESAMIN, METHODS OF MAKING AND USING THE SAME IN SKIN ANTI-AGING AND SKIN LIGHTENING APPLICATIONS

(71) Applicant: Access Business Group International LLC, Ada, MI (US)

(72) Inventors: Jatinder Rana, Grand Rapids, MI (US); Ganesh Diwakar, Ada, MI (US); Heidi Evenocheck, Grand Rapids, MI (US); Louise M. Schneider, Rockford, MI (US); Deepa Shenoy, Cypress, CA (US); John Rebhun, Greenville, MI (US); Samantha Roloff, Grand Rapids, MI (US); Jeffrey Scholten, Grand Rapids, MI (US); Jason N. Rothouse, Grand Rapids, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 187 days.

(21) Appl. No.: 15/085,691

(22) Filed: Mar. 30, 2016

(65) Prior Publication Data

US 2016/0287505 A1    Oct. 6, 2016

Related U.S. Application Data

(60) Provisional application No. 62/140,837, filed on Mar. 31, 2015.

(51) Int. Cl.

| *A61K 8/49* | (2006.01) |
| *A61K 8/66* | (2006.01) |
| *A61K 8/97* | (2017.01) |
| *A61K 9/00* | (2006.01) |
| *A61K 31/36* | (2006.01) |
| *A61K 45/06* | (2006.01) |
| *A61Q 19/00* | (2006.01) |
| *A61Q 19/02* | (2006.01) |
| *A61Q 19/08* | (2006.01) |

(52) U.S. Cl.
CPC .............. *A61K 8/4973* (2013.01); *A61K 8/66* (2013.01); *A61K 8/97* (2013.01); *A61K 9/0014* (2013.01); *A61K 31/36* (2013.01); *A61K 45/06* (2013.01); *A61Q 19/00* (2013.01); *A61Q 19/02* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| 2007/0166255 A1 | 7/2007 | Gupta |
| 2007/0254021 A1 | 11/2007 | Scimeca et al. |
| 2008/0103165 A1 | 5/2008 | Barlow et al. |
| 2008/0286394 A1 | 11/2008 | Pushpangadan et al. |
| 2010/0285154 A1 | 11/2010 | Hwang et al. |
| 2010/0305053 A1 | 12/2010 | Gueniche et al. |
| 2014/0378547 A1 | 12/2014 | Zielinski et al. |

FOREIGN PATENT DOCUMENTS

| JP | 2010013409 A | * | 1/2010 |
| WO | WO 20150852520 | * | 6/2015 |

OTHER PUBLICATIONS

International Search Report and Written Opinion received in International Application No. PCT/US2016/024944 dated Jul. 1, 2016.
Notification Concerning Transmittal and International Preliminary Report on Patentability received in International Application No. PCT/US2016/024944 dated Oct. 12, 2017.

* cited by examiner

*Primary Examiner* — Suzanne M Noakes
(74) *Attorney, Agent, or Firm* — Brinks Gilson & Lione

(57) ABSTRACT

Topical compositions, packaging systems and methods for improving the appearance of skin or at least one sign of aging in skin are described.

12 Claims, 5 Drawing Sheets

COMPOSITIONS INCLUDING SESAMIN, METHODS OF MAKING AND USING THE SAME IN SKIN ANTI-AGING AND SKIN LIGHTENING APPLICATIONS

RELATED APPLICATIONS

The present patent document claims the benefit of the filing date under 35 U.S.C. § 119(e) of Provisional U.S. Patent Application Ser. No. 62/140,837, filed Mar. 31, 2015, which is hereby incorporated by reference.

BACKGROUND

Topical compositions that include sesamin, optionally with at least one botanical extract and methods of use of the compositions to provide skin anti-aging and skin lightening effects are described. The disclosed compositions and methods may prevent, reduce, or reverse signs of premature aging, and/or improve the aesthetic appearance of skin. Use of the compositions may stimulate the skin's natural ability to recover from environmental stresses and prevent signs of premature aging as well as lighten the skin. The compositions include natural active ingredients derived from natural plant materials, as well as enzymes for repairing DNA damage.

The skin is made up of two major layers. The stratum corneum, or epidermis, is the top or outer layer of the skin. The primary function of the stratum corneum is to provide a protective covering and retard evaporative water loss from the aqueous interior. This is commonly referred to as the barrier function. The stratum corneum protects against mechanical insults, the ingress of foreign chemicals and assaults by microorganisms. It also provides the first defense against ultraviolet light, screening out more than 80% of incident ultraviolet B irradiation.

The dermis lies under the epidermis and makes up 90 percent of the skin's thickness. The dermis contains a dense meshwork of collagen and elastin, providing strength and elasticity to the skin. Fibroblasts constitute the main cell type present in the dermis. Fibroblasts are responsible for synthesis and secretion of dermal matrix components, including collagen, elastin, and glycosaminoglycans (such as hyaluronic acid). Whereas collagen provides strength to the skin and elastin its elasticity, glycosaminoglycans serve to keep the skin moist and plump.

To stay healthy, the skin must cope with changing environmental conditions, while simultaneously repairing damage. Environmental factors play a chief role in aging, wrinkles, skin discolorations and degenerative skin conditions. Exposure to sunlight and UV radiation are major factors resulting in skin damage, accounting for 90% of the symptoms of premature aging. Importantly, exposure to oxygen, sunlight, and other environmental or lifestyle stresses induces the formation of free-radicals. Free radicals can cause wrinkles by activating metalloproteases, such as collagenases, that are responsible for breaking down the skin's connective tissues (collagen and elastin). The result is premature aging. Free-radical damage can also cause a reduction in the thickness of the dermal layer. This can cause the skin to slacken. The slackening of the skin is the first and most visible sign of aging and a cause of wrinkles and lines.

Sunlight also can cause the accumulation of abnormal elastin by triggering the overproduction of metalloproteinases. Normally, metalloproteinases remodel sun-injured skin by manufacturing and reforming collagen. Repeatedly subjecting the skin to this imperfect rebuilding process may lead to formation of wrinkles or solar scars. Exposure to the sun also can rob the skin of essential moisture and create a stressed barrier that does not function properly. As moisture loss and irritation increase, the skin becomes sensitive, scaly, and dry.

Although oxygen and sunlight constitute the principal sources of free-radical damage, other contributors include cigarette smoke, environmental toxins, herbicides, pesticides, weather, diet, stress, sleep deprivation, excessive alcohol consumption, and pollution.

UV radiation from the sun may also damage DNA and may bring about several detrimental effects including cell death, mutation and neoplastic transformation. Studies indicate that some of these deleterious effects are due to the formation of two major classes of bipyrimidine DNA photoproducts, cyclobutane pyrimidine dimers (CPDs) and (6-4) photoproducts (6-4 PPs). Organisms have evolved several different pathways for removing CPDs and 6-4 PPs from cellular DNA. These pathways include various excision repair pathways which can be highly specific or non-specific for CPDs and 6-4 PPs.

In view of the many detrimental effects impacting the skin, there is a demand for cosmetic compositions and cosmetic methods for improving the appearance and condition of skin. Consumers seek "anti-aging" cosmetic products that treat or delay the visible signs of actual aging and weathered skin, such as wrinkles, lines, sagging, hyperpigmentation and age spots. Consumers also seek other benefits from cosmetic products in addition to anti-aging benefits. For example, the concept of "sensitive skin" has raised the demand for cosmetic products that improve the appearance and condition of sensitive, dry and/or flaky skin, and that soothe red, and/or irritated skin. Consumers also desire cosmetic products that treat spots, pimples, blemishes, and the like, or that reduce the risk of skin cancer.

In spite of the various anti-aging cosmetic products on the market for the treatment of skin, there remains a need for effective topically applied cosmetic compositions that provide anti-aging or rejuvenating benefits to the skin, hair and/or nails using natural ingredients as active components. Unnatural, chemically-synthesized products may be perceived as being environmentally or personally unsafe. In contrast, natural products are perceived as pure, mild, and superior to chemically synthesized products. Natural based products extracted from plants or herbs are believed to contain antioxidant/free-radical scavenging agents that can neutralize the effects of free-radical damage. Additionally, natural-based products can contain agents that stimulate the synthesis and restoration of damaged connective tissue structures in the dermis and barrier function in the epidermis.

However, delivering a cosmetic benefit from "natural" sources, such as plants or herbs, is not trivial. Deriving a real benefit from such sources requires identification of specific plant/herbal extracts or ingredients, their minimum active concentrations, and their additive or synergistic activities in combination with other ingredients to impart anti-aging and/or skin improvement benefits.

The present compositions further address the frequent irritation problems associated with exfoliating agents such as retinoids (e.g., tretinoin, retinol and retinal), carboxylic acids including α-hydroxy acids (e.g., lactic acid, glycolic acid), β-hydroxy acids (e.g., salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others. Exfoliants and other ingredients may also increase the skin's sensitivity to environmental conditions such as sunlight, wind, cold temperature and dry air, or may exacerbate the irritation attributable to a pre-existing skin disease.

The present invention therefore provides cosmetic compositions for topical use that have anti-aging, anti-oxidant, anti-irritant, anti-inflammatory, and/or aesthetic improvement properties.

SUMMARY

One embodiment relates to a topical composition that includes an amount of sesamin effective to improve the appearance of skin or at least one sign of aging in skin; and at least one pharmaceutically or cosmetically acceptable vehicle. The topical composition may further include at least one plant ingredient or a plant extract from *Pistacia, Leontopodium, Spirulina, Oroxylum, Schizandra, Moringa, Houttuynia, Isodon*, and *Saxifraga*, or mixtures thereof. The topical composition may further comprise at least one DNA repair enzyme. The at least one DNA repair enzyme may be a pyrimidine glycosylate/abasic lyase. The at least one DNA repair enzyme may be selected from the group consisting of a bacteriophage T4 pyrimidine dimer-specific endonuclease, a *Micrococcus luteus* N-glycosylase/AP lyase, a *Saccharomyces cerevisiae* N-glycosylase/apurinic-apyrimidinic lyase, a *Schizosaccharomyces pombe* UV damage endonuclease (UVDE), a *Chlorella* virus isolate PBCV-1 pyrimidine dimer-specific glycosylase, an *Anacystis nidulans* photolyase, and combinations thereof. The composition may be in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof. The at least one pharmaceutically or cosmetically acceptable vehicle may include one or more ingredients selected from the group consisting of water, a glycerin, a C1-C4 alcohol, a fatty alcohol, a fatty ether, a fatty ester, a polyol, a glycol, a vegetable oil, a mineral oil, a liposome, a laminar lipid material, a silicone oil, and combinations thereof. The composition may have a substantially neutral pH. The topical composition may further include a skin whitening agent selected from the group consisting of tyrosinase inhibitors, free radical scavengers, and mixtures thereof. In the topical composition the amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, effective to improve the appearance of skin or at least one sign of aging in skin can range from about 0.0001% to 5% by weight of the total composition. Alternatively, in the topical composition, the amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, effective to improve the appearance of skin or at least one sign of aging in skin can range from about 0.001% to about 0.5% by weight of the total composition. Alternatively, in the topical composition the amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, effective to improve the appearance of skin or at least one sign of aging in skin can range from about 0.01% to about 0.1% by weight of the total composition.

Another embodiment relates to a packaging system for improving the appearance of skin or at least one sign of aging in skin that includes one or more containers collectively containing the composition that includes an amount of sesamin effective to improve the appearance of skin or at least one sign of aging in skin and at least one pharmaceutically or cosmetically acceptable vehicle, and instructions for applying the composition from said one or more containers.

A further embodiment relates to a method of improving the appearance of skin or at least one sign of aging in the skin, the method comprising topically applying to the skin a composition in a cosmetically effective amount sufficient to improve the appearance of the skin or the at least one sign of aging in skin, wherein the composition comprises an amount of sesamin effective to improve the appearance of skin or at least one sign of aging in skin; and at least one pharmaceutically or cosmetically acceptable vehicle. In the method, the composition is in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof. In the method, at least one pharmaceutically or cosmetically acceptable vehicle includes one or more ingredients selected from the group consisting of water, a glycerin, a C1-C4 alcohols, a fatty alcohols, a fatty ethers, a fatty esters, a polyols, a glycols, a vegetable oils, a mineral oils, a liposomes, a laminar lipid materials, a silicone oils, and combinations thereof.

Another embodiment relates to a topical cosmetic composition for improving the appearance of skin or at least one sign of aging in the skin containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, where the improvement comprising an amount of sesamin effective to improve the appearance of skin or at least one sign of aging in skin.

Yet another embodiment relates to a method of modulating inducible nitric oxide synthase (iNOS) protein expression in skin cells comprising applying to a skin of a subject a composition in a cosmetically effective amount sufficient to modulate iNOS protein expression in skin cells, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, and at least one pharmaceutically or cosmetically acceptable vehicle.

Another embodiment relates to a method of activating peroxisome proliferator activator receptor gamma (PPARγ) in skin cells comprising applying to a skin a composition in a cosmetically effective amount sufficient to activate PPARγ in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof and at least one pharmaceutically or cosmetically acceptable vehicle.

A further embodiment relates to a method of decreasing a skin anti-inflammatory response comprising applying to the skin a composition in a cosmetically effective amount sufficient to decrease the skin anti-inflammatory response, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof and at least one pharmaceutically or cosmetically acceptable vehicle.

A further embodiment relates to a method of increasing superoxide dismutase (SOD) activity in a skin cell comprising applying to the skin a composition in a cosmetically effective amount sufficient to increase SOD activity in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof and at least one pharmaceutically or cosmetically acceptable vehicle.

A further embodiment relates to a method of stimulating or increasing matrix metalloproteinase (MMP) activity in a skin cell comprising applying to the skin a composition in a cosmetically effective amount sufficient to stimulate or increase matrix metalloproteinase activity in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof and at least one pharmaceutically or cosmetically acceptable vehicle.

Yet further embodiment relates to a method of increasing antioxidant responsive elements (AREs) response in a skin cell comprising applying to the skin a composition in a cosmetically effective amount sufficient to increase ARE response in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof and at least one pharmaceutically or cosmetically acceptable vehicle.

Yet further embodiment relates to a method of increasing skin lightening comprising applying to the skin a composition in a cosmetically effective amount sufficient to increase skin lightening, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, and at least one pharmaceutically or cosmetically acceptable vehicle.

DETAILED DESCRIPTION

Figure 1:
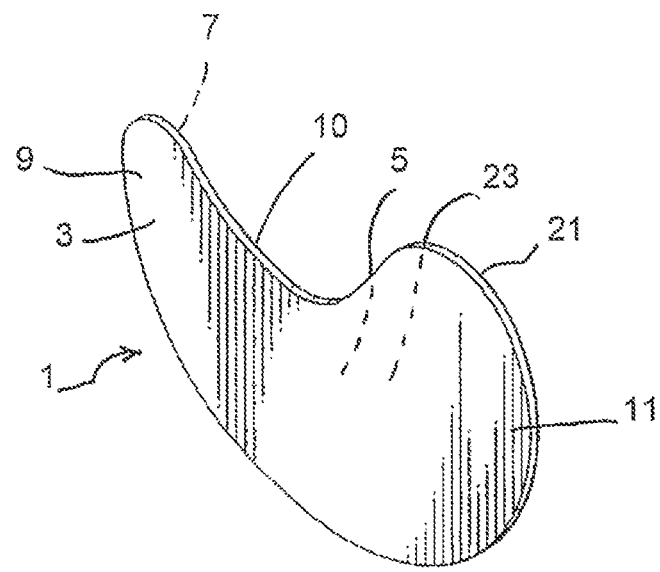
FIG. 1 shows a representative patch for treating an area around the eye.

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention is based on the surprising discovery that a plant ingredient (e.g., sesamin) or plant extract of *Sesamum*, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, provides an anti-aging skin effect and/or improved aesthetic appearance as well as extending youthfulness of the skin effect. Also, the present invention is based on the surprising discovery that a plant ingredient or plant extract of *Sesamum*, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, (i) modulates inducible nitric oxide synthase (iNOS) protein expression in a skin, (ii) activates peroxisome proliferator activator receptor gamma (PPARγ)(and thus regulates fatty acid storage glucose metabolism) in skin cells, (iii) decreases a skin anti-inflammatory response, increasing superoxide dismutase activity in a skin, (iv) increases anti-oxidant response elements (ARE), and (v) stimulates or increases matrix metalloproteinase activity. The ingredient or extract may be from any species members of these genus groups. In certain embodiments, when a combination of plant ingredients or plant extracts is used, the anti-aging skin effect may be at least additive, and preferably synergistic, as compared to the effect of the individual botanical components. Accordingly, compositions that include a plant ingredient or plant extract of *Sesamum* and, optionally, at least one plant ingredient or plant extract from *Pistacia, Leontopodium, Spirulina, Oroxylum, Schizandra, Moringa, Houttuynia, Isodon*, and *Saxifraga*, or mixtures thereof, in sufficient amounts to achieve an anti-aging skin effect and their use are described.

The term "composition" refers to a product that treats, improves, promotes, increases, manages, controls, maintains, optimizes, modifies, reduces, inhibits, or prevents a particular condition associated with a natural state, biological process or disease or disorder. For example, a composition improves at least one sign of aging and/or improves the appearance of skin, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment.

As used herein, the term "extract" or "botanical extract" refers to a solid, viscid, or liquid substance or preparation that includes an active ingredient(s) of a substance of plant, such as *Sesamum* (e.g., *Sesamum indicum*), *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) in a concentrated form. The term "extract" is intended to include not only a crude extract produced from *Sesamum* (e.g., *Sesamum indicum*), *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*); by use of a solvent selected from among water, lower alcohols of 1 to 4 carbon atoms, such as methanol, ethanol, butanol, etc., ethylene, acetone, hexane, ether, chloroform, ethylacetate, butylacetate, dichloromethane, N,N-dimethylformamide (DMF), dimethylsulfoxide (DMSO), 1,3-butylene glycol, propylene glycol and a combination thereof, but also a fraction of the crude extract in such a solvent. So long as it assures the extraction and preservation of the active ingredient(s), any extraction method may be employed. Examples of botanical extracts include extracts from *Sesamum* (e.g., *Sesamum indicum*), *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*).

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving at least one sign of aging and/or improving the appearance of skin, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

"Improving at least one sign of aging" and "improving a sign of aging" are used interchangeably herein to designate preventing, arresting, reversing, ameliorating, diminishing, and/or reducing a sign of aging. Representative signs of aging include, but are not limited to, lines, fine lines, wrinkles, crow's feet, dark eye circles, blemishes, age spots, stretch marks, or combinations thereof.

"Improving the appearance of skin" and "improving the aesthetic appearance of skin" are used interchangeably herein to designate an aesthetic improvement in the appearance of skin. Representative improvements may include, but are not limited to, favorable characteristics and/or properties related skin thickness, elasticity, resiliency, moisturization, smoothness, tone, texture, radiance, lightness (i.e., skin lightening), luster, brightness, clarity, contour, firmness, tautness, suppleness, softness, sensitivity, pore size, or combinations thereof. These terms may also be used to designate an improvement in an adverse skin condition. Representative adverse conditions affecting by, resulting in or resulting from such an adverse skin condition include, but are not limited to, psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, tactile roughness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer," "administered," "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In preferred embodiments, topical routes of administering a composition are suitable.

The terms "modulate" or "regulate" refer to ability of sesamin, individually or in combination with at least one botanical extract of *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) to stimulate, increase, decrease, and/or inhibit at least one of (i) activity or expression of a protein (e.g., an enzyme such as inducible nitric oxide synthase (iNOS), superoxide dismutase (SOD), matrix metalloproteinase(s), and/or peroxisome proliferator activator receptor gamma (PPAR), or (ii) a downstream effect (e.g., fatty acid storage glucose metabolism, or skin cell inflammatory response).

The terms "reduce," "reducing," "inhibit" or "inhibiting" refer to a decrease or reduction in protein activity and/or expression, and/or its dowstream effect, in the presence of a plant ingredient or plant extract of *Sesamum* (*Sesamum indicum*; "sesamin"), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), when compared to protein activity and/or expression in the absence of a plant ingredient or plant extract of *Sesamum* (*Sesamum indicum*), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), such as in a control sample. The degree of decrease or inhibition of protein activity and/or expression, and/or its downstream effect, will vary with the nature and quantity of a plant ingredient or plant extract of *Sesamum* (*Sesamum indicum*), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) present, but will be evident e.g., as a detectable decrease in protein activity and/or expression; desirably a degree of decrease greater than 10%, 25%, 50%, 75%, 90%, 95% or 99% as compared to protein activity and/or expression in the absence of sesamin, individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*).

The terms "increase," "increasing," or "stimulate" refer to an increase in in protein activity and/or expression, and/or its dowstream effect, in the presence of a plant ingredient or plant extract of *Sesamum* (*Sesamum indicum*; "sesamin"), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), when compared to protein activity and/or expression in the absence of a plant ingredient or plant extract of *Sesamum* (*Sesamum indicum*), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), such as in a control sample. The degree of increase of protein activity and/or expression, and/or its dowstream effect, will vary with the nature and quantity of a plant ingredient or plant extract of *Sesamum* (*Sesamum indicum*), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum lum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) present, but will be evident e.g., as a detectable increase in protein activity and/or expression; desirably a degree of increase greater than 10%, 25%, 50%, 75%, 90%, 95% or 99% as compared to protein activity and/or expression in the absence of a plant ingredient or plant extract of *Sesamum* (*Sesamum indicum*), individually or in combination with at least one plant ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*).

As used herein, the term "subject" or "individual" includes mammals to which a composition may be administered. Non-limiting examples of mammals include humans, non-human primates, rodents (including transgenic and non-transgenic mice) or the like. In some embodiments, the subject is a mammal, and in some embodiments, the subject is human.

The present invention provides a cosmetic treatment system having a topical composition including a plant ingredient, plant extract or a natural complex of *Sesamum* (e.g., *Sesamum indicum*; "sesamin"), individually or in combination with at least one plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof; and a pharmaceutically or cosmetically acceptable vehicle. In certain embodiments, when a combination of plant ingredients or plant extracts is used, the desired effect may be at least additive, and preferably synergistic, as compared to the effect of the individual botanical components.

Sesamin is a lignan that can be isolated from *Sesamum* (e.g., *Sesamum indicum*), bark of Fagara plants and from sesame oil. Most wild species of the genus *Sesamum* are native to sub-Saharan Africa. The cultures *Sesamum indicum* originated in India. The botanical name of sesamin is *Sesamum indicum*; commonly known as sesamin, fagarol, sezamin or asarinin. Sesamin is commercially available from, e.g., Virun Chemicals. The term "sesamin" means a plant ingredient or plant extract or a natural complex isolated from *Sesamum* (e.g., *Sesamum indicum*).

The structure of sesamin is shown below:

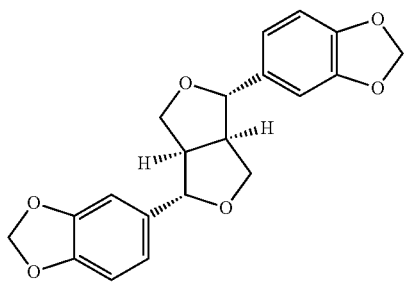 [SMILES: c1cc2c(cc1[C@H]1OC[C@H]3[C@@H]1CO[C@@H]3c1ccc3c(c1)OCO3)OCO2]

The botanical extracts of *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) may be commercially obtained from various sources including Barnet Products Corp, Englewood Cliffs, N.J.; Maruzen Pharmaceuticals Co. Ltd, Onomichi-City Hiroshima, Japan; and DSM, Heerlen (NL). In addition, a suitable plant ingredients and botanical extracts of *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa ptery-* gosperma), *Houttuynia* (e.g., *Houttuynia cordata*), *Isodon* (e.g., *Isodon japonicus*), and *Saxifraga* (e.g., *Saxifraga stolonifera*) may be obtained using any of the extraction and purification techniques discussed more fully below or known in the art.

In one example, a botanical extract useful in the unique compositions of the present invention might be obtained using an organic solvent extraction technique.

In another example, solvent sequential fractionation may be used to obtain a botanical extract useful in the unique compositions of the present invention.

Total hydro-ethanolic extraction techniques may also be used to obtain a botanical extract useful in the unique compositions of the present invention. Generally, this is referred to as a lump-sum extraction. The botanical extract generated in this process will contain a broad variety of phytochemicals present in the extracted material including fat and water solubles. Following collection of the botanical extract solution, the solvent will be evaporated, resulting in the botanical extract.

Total ethanol extraction may also be used in the present invention. This technique uses ethanol, rather than hydro-ethanol, as the solvent. This extraction technique generates an extract that may include fat soluble and/or lipophilic compounds in addition to water soluble compounds.

Another example of an extraction technique that may be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August: 48(8):3408-12; Hong et al., "Microwave-assisted extraction of phenolic compounds from grape seed." *Nat Prod Lett* 2001; 15(3):197-204; Ashraf-Khorassani et al., "Sequential fractionation of grape seeds into oils, polyphenols, and procyanidins via a single system employing $CO_2$-based fluids." *J. Agric Food Chem.*, 2004 May 5; 52(9):2440-4.

Application of the topical composition of the present invention may improve the aesthetic appearance of the skin, and may rejuvenate or enhance the skin. The compositions of the present invention may also provide a variety of anti-aging and skin texture benefits. It is believed a composition comprising sesamin, individually or in combination with at least one botanical ingredient or extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) provides significant anti-aging and skin texture benefits relative to other commercially available skin anti-aging topical products. Topical application of the ingredient or combinations of ingredients may produce benefits that are additive or synergistic relative to application of the individual ingredients therein. The terms "synergistic benefit," "synergistic effect," or "synergizing effect" are defined herein as the interaction of two or more combination compositions (e.g., an extract mixture) to produce a combined biological effect(s) or benefit(s) greater than the sum of their separate effects (i.e., 1+1<2 or 1+1+1<3). The synergistic effect can be about or greater than about 10, 20, 30, 50, 75, 100, 120, 150, 200, 250, 350, or 500% or even more than the summed (additive) effect of each composition. The effect can be any of the measurable effects described herein. The term "additive benefit" refers to a combined biological effect(s) or benefit(s) equal to the sum of two or more combination compositions (e.g., an extract mixture) separate effects.

The composition comprising sesamin provides benefits to skin relating to anti-aging and improved aesthetic appearance. Accordingly, certain embodiments relate to topical compositions and methods for their use in treating skin to prevent, arrest, reverse, ameliorate, diminish, reduce or improve signs of aging, including, or associated with, chronological aging, hormonal aging, and/or photoaging. The signs of aging may include, but are not limited to, skin fragility; loss of collagen and/or elastin; estrogen imbalance in skin; skin atrophy; appearance and/or depth of lines and/or wrinkles, including fine lines; skin discoloration, including dark eye circles; crow's feet; skin sagging; skin fatigue and/or stress, e.g., skin breakout due to environmental stress, such as pollution and/or temperature changes; skin dryness, fine lines due to skin dryness, skin roughness; skin flakiness; cellular aging; loss of skin tone, elasticity, clarity, luminosity, and/or luster; loss of skin firmness; poor skin texture; loss of skin elasticity and/or resiliency; thin skin, and inflammation.

The benefits and improvements to the aesthetic appearance of skin can be manifested in any of the following: reduction in pore size, fine lines, wrinkles, tactile roughness, and inflammation; improvement in skin tone, radiance, clarity and/or tautness; promotion of anti-oxidant activity; improvement in skin firmness, plumpness, suppleness, and/or softness; improvement in procollagen and/or collagen production; improvement in skin texture and/or promotion of retexturization; improvement in skin barrier repair and/or function; improvement in appearance of skin contours; restoration of skin luster, clarity, and/or brightness; replenishment of essential nutrients and/or constituents in the skin decreased by aging and/or menopause; improvement in communication among skin cells; increase in cell proliferation and/or multiplication; increase in skin cell metabolism decreased by aging and/or menopause; improvement in skin moisturization; promotion and/or acceleration of cell turnover; enhancement of skin thickness; increase in skin elasticity and/or resiliency; and enhancement of exfoliation, with or without the use of alpha or beta hydroxy acids, keto acids or other exfoliants.

Other benefits may include an increase in skin smoothness and/or softness, an increase in the perception of skin condition, an increase in skin moisture, a reduction in skin stress and fine lines, an increase in brightness and/or lightening, improved skin texture and skin firmness.

In one embodiment of the present invention, the topical composition includes sesamin in the amount sufficient to provide benefits to skin relating to anti-aging and improved aesthetic appearance; and a pharmaceutically or cosmetically acceptable vehicle. Specifically, sesamin is present in an amount ranging from about 0.0001% to 5% by weight of the total composition, desirably from about 0.001 wt % to about wt 0.5%, more desirably from about 0.01 wt % to about 0.1 wt %.

The compositions including a plant ingredient, a plant extract or a natural complex of *Sesamum* may also include a plant ingredient or plant extract from *Pistacia, Leontopodium, Spirulina, Oroxylum, Schizandra, Moringa, Houttuynia, Isodon,* and *Saxifraga*, or mixtures thereof. The ingredient or extract may be from any species members of these genus groups.

Certain other embodiments relate to a the topical composition that includes sesamin in combination with at least one other plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof in the amounts sufficient to provide benefits to skin relating to anti-aging and improved aesthetic appearance; and a pharmaceutically or cosmetically acceptable vehicle.

In a particular embodiment, the topical composition may include sesamin in combination with *Pistacia* (e.g., *Pistacia lentiscus*). *Pistacia* is a genus of flowering plants in the cashew family, Anacardiaceae. It contains 10 to 20 species. Active ingredients of *Pistacia* are believed to include phenolic compounds, flavonoids and tannins with an antioxidant activity. Consequently, use of *Pistacia* ingredients or extracts may provide enhanced benefits to skin relating to anti-aging and improved aesthetic appearance.

In a particular embodiment, the topical composition may include sesamin in combination with *Leontopodium* (e.g., *Leontopodium alpinium*). *Leontopodium alpinum* is an herbaceous plant of the family Asteraceae which grows spontaneously on mountain ranges from the Pyrenees and the Alps to the Himalayas. Previous scientific studies have demonstrated the presence in the plant of powerful antioxidants and other substances with both anti-inflammatory and cytoprotective properties. These include the natural actives, leontopodic acids A and B, chlorogenic acid, and 3,5-dicaffeoylquinic acid, which have anti-hyaluronidasic and anti-collagenasic activity. Also, present are phytosterols, amino acids, polysaccharides with moisturizing properties and which act as plant nutrients. *Leontopodium alpinum* has skin care benefits and exhibits strong anti-oxidant, anti-hyaluronidasic and anti-collagenasic activity. Consequently, use of *Leontopodium* ingredients or extracts may provide enhanced benefits to skin relating to anti-aging and improved aesthetic appearance.

In a particular embodiment, the topical composition may include sesamin in combination with *Spirulina* (e.g., *Spirulina platensis*). *S. platensis*, planktonic is a blue-green microalgae that contains phycobiliproteins (phycocyanin and allophycocyanin). A protean extract of *S. platensis* is a potent free-radical scavenger (hydroxyl and peroxyl radicals) and inhibits microsomal lipid peroxidation. *S. platenis* has antioxidant activity due to presence of biliprotein phycocyanin. Consequently, use of *Spirulina* ingredients or extracts may provide enhanced benefits to skin relating to anti-aging and improved aesthetic appearance.

In a particular embodiment, the topical composition may include sesamin in combination with *Oroxylum* (e.g., *Oroxylum indicum*). *Oroxylum indictum* is a species of flowering plant belonging to the family Bignoniaceae, commonly called midnight horror, *oroxylum*, kampong, or Indian trumpet flower. The leaf contains chrysin and baicalein. The flavonoid baicalein was found as an active component in the extract. Tetuin, the 6-glucoside of baicalein, is reported in the seeds. Oroxindin has also been isolated from *Oroxylum indicum* whereas oroxylin A is reported in the root bark. Other flavonoids, having anti-inflammatory and anti-allergy effects, are also present. Consequently, use of *Oroxylum* ingredients or extracts may provide enhanced benefits to skin relating to anti-aging and improved aesthetic appearance.

In a particular embodiment, the topical composition may include sesamin in combination with *Schizandra* (e.g., *Schizandra chinensis*). *Schizandra* is a deciduous woody vine native to forests of Northern China and the Russian Far East. Its berries are used in traditional Chinese medicine, where it is considered one of the 50 fundamental herbs. They are most often used in dried form, and boiled to make a tea. Chemical constituents include the lignans: schizandrin, deoxyschizandrin, gomisins, and pregomisin, which are found in the seeds of the fruit. Two major lignans, schizandrin and gomisin A, have been shown to induce interleukin (IL)-8, macrophage inflammatory protein-1β, and granulocyte-macrophage-colony stimulating factor (GM-CSF) release by THP-1 cells. Therefore, *S. Chinensis* may be therapeutically beneficial in promoting the body's humoral and cell-mediated immune responses. Schizandrin is one of the main dibenzocyclooctadiene lignans present in the fruit of *Schizandra chinensis*. In vitro biological activities including hepatoprotective, antiviral and neuroprotective effects of schizandrin and other dibenzocyclooctadiene lignans have been reported. Recent studies have demonstrated that schizandrin exhibits anti-oxidative effects in mice. Other chemical constituents include schisandrin B, γ-terpinene, bisabolene (+)-gomisin K2, gomisin S, pregomisin, schisantherin A, schicantherin B, angeloylgomisin Q, and rubrildilactione. Consequently, use of *Schizandra* ingredients or extracts may provide enhanced benefits to skin relating to anti-aging and improved aesthetic appearance.

In a particular embodiment, the topical composition may include sesamin in combination with *Moringa* (e.g., *Moringa pterygosperma, Moringa oleifera*). *Moringa* is a plant that is native to the sub-Himalayan areas of India, Pakistan, Bangladesh, and Afghanistan. It is also grown in the tropics. The leaves, bark, flowers, fruit, seeds, and root are used to make medicine. *Moringa oleifera* is the most widely cultivated species of the genus *Moringa*, which is the only genus in the family Moringaceae. English common names include: *moringa*, drumstick tree (from the appearance of the long, slender, triangular seed-pods), horseradish tree (from the taste of the roots, which resembles horseradish), ben oil tree, or benzoil tree (from the oil which is derived from the seeds). *Moringa* is used for "tired blood" (anemia), arthritis and other joint pain (rheumatism), asthma, cancer, constipation, diabetes, diarrhea, epilepsy, stomach pain, stomach and intestinal ulcers, intestinal spasms, headache, heart problems, high blood pressure, kidney stones, fluid retention, thyroid disorders, and bacterial, fungal, viral, and parasitic infections. *Moringa* is also used to reduce swelling, increase sex drive (as an aphrodisiac), prevent pregnancy, boost the immune system, and increase breast milk production. Some people use it as a nutritional supplement or tonic. *Moringa* is sometimes applied directly to the skin as a germ-killer or drying agent (astringent). It is also used topically for treating pockets of infection (abscesses), athlete's foot, dandruff, gum disease (gingivitis), snakebites, warts, and wounds. Oil from *Moringa* seeds is used in foods, perfume, and hair care products, and as a machine lubricant. *Moringa* contains proteins, vitamins, and minerals. Chemical constituents of *Moringa* include quercetin and kaempferol type glycosides, having antioxidant properties, seem to help protect cells from damage. Consequently, use of *Moringa* ingredients or extracts may provide enhanced benefits to skin relating to anti-aging and improved aesthetic appearance.

In a particular embodiment, the topical composition may include sesamin in combination with *Houttuynia* (e.g., *Houttuynia cordata*). *H. cordata* is a Chinese medicinal herb that is found throughout Eastern Asia. *H. cordata* is used in folk medicine for diuresis and detoxification and herbal medicine for its antiviral, antibacterial and antileukemic activities. *H. cordata* was used by Chinese scientists to tackle SARS, as it is conventionally used to treat pneumonia. *H. cordata* injection, a traditional Chinese medicine, is often used to relieve abnormal lung symptoms, infectious disease, refractory hemoptysis, and malignant pleural effusion in China. Its injection has a direct inhibitory activity against pseudorabies herpes virus in vitro. *H. cordata* contains decanoyl acetaldehyde compounds that have antibiotic, antivirus, and fungal inhibition effects and flavonoid-series compounds that show diuretic, cardiac, and evacuation effects. Other chemical constituents include quercetin derivatives and chlorogenic acid. Use of *Houttuynia* ingredients or extracts may provide enhanced benefits to skin relating to anti-aging and improved aesthetic appearance.

In a particular embodiment, the topical composition may include sesamin in combination with *Isodon* (e.g., *Isodon japonicus*). *Isodon japonicus* is a perennial member of the *Isodon* genus in the family Labiatae and is typically used medicinally in the treatment of stomach cancer. The ingredients of the *I. japonicus* extract include ent-kaurane diterpenoids that have anti-inflammation effects and NF-kB target gene inhibitory effects. Consequently, use of *Isodon* ingredients or extracts may provide enhanced benefits to skin relating to anti-aging and improved aesthetic appearance.

In a particular embodiment, the topical composition may include sesamin in combination with *Saxifraga* (e.g., *Saxifraga stolonifera*). *Saxifraga stolonifera*, an evergreen dicotyledon, has been identified as an important resource in Chinese medicine due to its anticancer activity. Saxifrage is often called "yuki no shita" in Japanese and means "under the snow." There are several theories as to the meaning of the name of this plant. One says that the name means that its leaves can grow in winter even "under the snow" while another means its flowers are white in color just like snow. Japanese people often consider snow as a symbol of whiteness, so when praising a woman on having a beautiful white skin, the expression "just like snow" is often used. Chemical components isolated from ethanol extracts of *S. stolonifera* plant include n-C(31)H(64), (n-C(17)H(35))(2)CO, beta-sitosterol, n-C(29)H(60), Bergenin, Protocatechuic acid, Gallic acid, Quercitrin 3-O-alpha-1-rhamnoside, Quercetin, and Quercetin 3-O-beta-d-glucopyranoside. Consequently, use of *Saxifraga* ingredients or extracts may provide enhanced benefits to skin relating to anti-aging and improved aesthetic appearance.

The plant ingredients or plant extracts in combination with sesamin for use in the present invention are generally present in the composition, individually or collectively, in an amount ranging from about 0.0001% to 5% by weight of the total composition, desirably from about 0.001 wt % to about wt 0.5%, more desirably from about 0.01 wt % to about 0.1 wt %.

A particularly preferred embodiment relates to a cosmetic treatment system utilizing a topical composition suitably formulated for treatment of the area around the eyes. While not wishing to be bound by theory, it is believed treatment of the eye area can be improved when using a patch impregnated with a composition comprising sesamin, individually or in combination with at least one plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof.

The plant ingredients or plant extracts for use in the present invention are generally present in a collective amount ranging from about 0.0001% to 5% by weight of the total composition, desirably from about 0.001 wt % to about wt 0.5%, more desirably from about 0.01 wt % to about 0.1 wt %.

The present invention may include a plant ingredient or plant extract from plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*) (or mixtures thereof), where the at least one plant ingredient or plant extract is present in the composition, individually or collectively, in an amount ranging from about 0.001% to about 10% by weight of the total composition, desirably from about 0.005 wt % to about 2 wt %, more desirably from about 0.02 wt % to about 0.08 wt %.

The compositions may have a pH between about 6.0 to about 8.0, or alternatively the composition may have a pH that is substantially neutral. In certain embodiments, the compositions in which the botanical extract is used have a generally neutral pH.

In certain other embodiments, the composition of the present invention can further include DNA repair enzymes. DNA repair enzymes for use in the present invention may include enzymes involved in either the base excision repair (BER), the nucleotide excision repair (NER) pathway, or alternate excision repair pathways as described in e.g., U.S. Pat. No. 6,368,594. These pathways are mediated by separate sets of proteins capable of carrying out DNA incision, lesion removal, gap-filling, and ligation reactions.

The NER pathway constitutes a widely distributed, lesion non-specific repair pathway orchestrating DNA damage removal via a dual incision reaction upstream and downstream from the damage site resulting in release of an oligonucleotide containing the damage. Following removal of the damaged DNA, the resulting gap is filled and the DNA ends are ligated together.

The BER pathway is the primary defense against all major forms of DNA base damage. This pathway is responsible for detecting and removing a variety of specific, individual base lesions within a large pool of undamaged DNA. BER pathways typically involve the activity of N-glycosylase/AP lyase enzymes specific for CPDs. The N-glycosylase/AP lyase enzymes first cleave the N-glycosidic bond of a CPD 5' pyrimidine and then cleave the phosphodiester backbone at an abasic site via a β-lyase mechanism.

Suitable DNA repair enzymes for use in the present invention have N-glycosylase/AP lyase activities capable of recognizing, excising and repairing damaged DNA, such as CPDs and (6-4) photoproducts. The activity of these enzymes can be light-dependent (e.g., photolyases) or light-independent. Exemplary DNA repair enzymes in this group include, but are not limited to, bacteriophage T4 pyrimidine dimer-specific endonuclease (denV endonuclease), *Micrococcus luteus* N-glycosylase/AP lyase, *Saccharomyces cerevisiae* N-glycosylase/apurinic-apyrimidinic lyase, *Schizosaccharomyces pombe* UV damage endonuclease (UVDE), *Chlorella* virus isolate PBCV-1 pyrimidine dimer-specific glycosylase, *Anacystis nidulans* photolyase, and modified, non-native (e.g., recombinant) enzyme products thereof.

DNA repair enzymes may also include other members from the BER, NER or alternate pathways. These enzymes may include $O^6$-methylguanine-DNA methyltransferases, uracil- and hypoxanthine-DNA glycosylases, DNA exonucleases, damaged-bases glycosylases (e.g., 3-methyladenine-DNA glycosylase), endonucleases alone or in complexes (e.g., *E. coli* uvrA/uvrB/uvrC endonuclease complex), and other enzymes and enzyme complexes whose activities at present are only partially understood, such as, the products of the ERCC genes of humans and the RAD genes of yeast. Exemplary DNA repair enzymes include, but are not limited to, uracil DNA glycosylases, 3-methyladenine DNA glycosylase, Endonuclease III/thymine glycol DNA glycosylases, Endonuclease VIII, fapy/8-oxoguanine DNA glycosylases, A-G-mismatch DNA glycoslyases, G-T mismatch DNA glycosylases, formyluracil DNA glycosylases, hydroxymethyl uracil DNA glycosylases, XPC-hHR23B, XPA, RPA, XPB, TFIIH, XPG, XPF-ERCC1, Rad-4-Rad23, Rad14, Rfa, Rad25/Ss12, Rad3, Rad2, Rad1-Rad10, various DNA polymerases, DNA ligases and the like. Exemplary sources for these enzymes may include bacterial or mammalian cell sources, including, but not limited to *E. coli, S. cerevisiae, S. pombe*, human, human, monkey, mouse, rat, hamster and the like.

As used herein, the term "DNA repair enzyme" is intended to include the foregoing enzymes and other enzymes now known or subsequently discovered or developed, including glycosylases, apurinic/apyrimidinic endonucleases or other enzymes having activities capable of repairing damaged DNA.

DNA repair enzymes may be derived or extracted from suitable sources such as *E. coli, Micrococcus*, and the like. The DNA repair enzymes may be encapsulated in liposomes as described in U.S. Pat. No. 5,296,231, the entire content of which is incorporated herein by reference. For example, a DNA repair enzyme derived from a *Micrococcus luteus* cell lysate is provided in a liposomal formulation containing lecithin and water and is available as ULTRASOMES™ from Applied Genetics, Inc. Dermatics, Freeport, N.Y. or ULTRASOMES-V™ from Barnet Products Corporation, Englewood Cliffs, N.J. Liposomes encapsulating an *Anacystis nidulans* lysate containing the *Anacystis nidulans* photolyase are available as PHOTOSOMES™ or PHOTOSOMES-V™ from Applied Genetics, Inc. Dermatics, (Freeport, N.Y.). The liposomes may include conventional phospholipids, oleic acid and/or cholesterol hemisuccinate from vegetable-derived sources, e.g., soybean or they may be produced from other suitable sources conventionally known to those skilled in the art.

Exemplary embodiments may incorporate ULTRASOMES™, ULTRASOMES-V™, PHOTOSOMES™, or PHOTOSOMES-V™ in an amount ranging from about 0.01% to 20% by weight of the total composition, desirably from about 0.1 wt % to about wt 10%, more desirably from about 0.5 wt % to about 3 wt %.

Liposomes may be used as delivery agents to facilitate transfer of cosmetically active agents into the dermis of skin, such as the DNA repair enzymes or the plant or botanical ingredients of the present invention. Other delivery agents may be used for dermal delivery in place of the liposomes, including, but not limited to skin delivery vehicles known to those skilled in the art, including emulsions, microemulsions, nanoemulsions, nanoparticles, microspheres, ethosomes, transfersomes, and niosomes.

In certain embodiments, additional cosmetic ingredients may also be included in the cosmetic composition, including, but not limited to, ingredients present in: licorice, licorice extracts, licorice derivatives (e.g., glycyrrhizinates); lemon extract; cucumber extract; sunflower seed extract; castor seed oil; oat proteins, oat extracts, hydrolyzed oats; silk protein (e.g., sericin); hyaluronic acid and its derivatives (e.g., sodium hyaluronate); vitamins; minerals; anti-oxidants; phospholipids, sphingolipids, cholesterol; and/or other ingredients or combinations thereof having anti-aging, anti-oxidant, anti-inflammatory, anti-irritant, anti-cancer or other skin-protective properties; aesthetic appearance enhancing properties; and/or increased skin delivery properties.

Cosmetically useful vitamins, minerals and/or anti-oxidants for topical application in accordance with the present invention include plant ingredients and extracts having anti-oxidant properties (e.g., Rosemary extract, Centella asiaticoside, etc.); vitamin A and its precursors or derivatives (e.g., beta-carotene, retinyl palmitate); vitamin B3 and its precursors or derivatives (e.g., niacinamide); vitamin B5 and its precursors or derivatives (e.g. panthenol); vitamin C and its precursors or derivatives (e.g., tetrahexyldecyl ascorbate, ascorbyl palmitate); vitamin E and its precursors or derivatives (e.g., d-alpha-tocopherol, tocopheryl acetate); vitamin K and its precursors or derivatives; selenium and its derivatives (e.g., L-selenomethionine); and alpha lipoic acid (ALA).

ALA is a potent, naturally occurring anti-oxidant, sometimes referred to as the "universal anti-oxidant" because of its activity and solubility in both water and lipids. ALA is able to penetrate into skin cells, is able to prevent activation of the proinflammatory NF-kB pathway responsible for breakdown of collagen and elastin, and is able to boost the protective effects of vitamins E and C, thereby boosting naturally occurring anti-oxidants within cells.

In one embodiment, tetrahexyldecyl ascorbate may be incorporated in the composition of the present invention. Tetrahexyldecyl ascorbate is a stable, lipid-soluble ester derivative of vitamin C. Vitamin C has been reported to promote collagen synthesis, inhibit lipid breakdown, regenerate vitamin E, reduce fine lines and wrinkles, heal sunburns, and is a potent anti-oxidant scavenger of free radicals having significant anti-inflammatory properties, hindering production of e.g., arachidonic acid.

In another embodiment, panthenol or its equivalents are contemplated for use with the composition. Panthenol is an effective film-forming moisturizing agent having anti-inflammatory properties. Panthenol equivalents may include alcohol derivatives of pantothenic acid, such as the ones described in CTFA Cosmetic Ingredient Handbook, The Cosmetic, Toiletry and Fragrance Association. Inc., pp. 272-273, 1992. For optimal usefulness, the amount of panthenol should be chosen so that the composition dries reasonably quickly. The more panthenol in the composition, the longer it takes for the composition to dry when it is applied to skin or other surfaces.

Vitamins, minerals, and/or anti-oxidants may be present in a collective amount ranging from about 0.01% to 20% by weight of the total composition, desirably from about 0.1 wt % to about wt 10%, more desirably from about 0.5 wt % to about 3 wt %.

Optionally, the present composition may additionally include one or more anesthetics, anti-allergenics, anti-irritants, antifungals, anti-microbials, anti-inflammatory agents, antiseptics, chelating agents, colorants, depigmenting agents, emollients, emulsifiers, film formers, fragrances, humectants, insect repellents, lubricants, moisturizers, pharmaceutical agents, photostabilizing agents, preservatives, skin protectants, skin penetration enhancers, sunscreens, stabilizers, surfactants, thickeners, viscosity modifiers, or any combinations thereof.

Certain embodiment relate to plant or botanical ingredients and natural, active ingredients having anti-irritant or anti-inflammatory properties to counter potential irritation to skin. Although some embodiments lack the use of exfoliating agents, these agents may be included provided that sufficient anti-irritant/anti-inflammatory agents are included to ameliorate the irritating effects of exfoliating agents. Exemplary anti-irritants include, but are not limited to, aloe vera, α-bisabolol, caffeine or other xanthenes, chamomile, cola nitada extract, dipotassium glycyrrhizinate, glycyrrhizic acid and its derivatives, green tea extract, lecithin or hydrogenated lecithin, licorice extract, tea tree oil, steroidal or non-steroidal anti-inflammatory agents, including, but not limited to cyclooxygenase inhibitors (e.g., salicylic acid, acetylsalicylic acid), NF-κB inhibitors, strontium acetate, strontium chloride, strontium nitrate, urea, or combinations thereof. Desirable anti-irritants may include dipotassium glycyrrhizinate, lecithin and hydrogenated lecithin.

Anti-irritant or anti-inflammatory agents may be present individually or collectively in an amount ranging from about 0.01% to 10% by weight of the total composition, desirably from about 0.05 wt % to about 5 wt %, more desirably from about 0.2 wt % to about 1.5 wt %.

The plant ingredients, plant extracts, oils, vitamins, minerals, antioxidants, anti-irritants or other active agents may be included, either individually or collectively, in a pharmaceutically or cosmetically acceptable vehicle. Examples of pharmaceutically or cosmetically acceptable vehicles suitable for the embodiments of the present invention include, but are not limited to, water, C1-C4 alcohols, fatty alcohols, fatty ethers, fatty esters, glycerin, glycols, vegetable oils, mineral oils, lecithin, hydrogenated lecithin, liposomes, laminar lipid materials, phospholipids, polyglycols, polyols, propyl alcohol, silicone oils, vegetable oil, or any combinations thereof.

The pharmaceutically or cosmetically acceptable vehicle for use with the compositions of the present invention may be in the form of a homogeneous phase formulation or in the form of an emulsion or microemulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semi-solid (such as gel and stick); and aqueous based gel and mousse system.

The pharmaceutically or cosmetically acceptable vehicle will usually contain from about 5% to about 99.9% by weight of the total composition, desirably from about 25% to about 80%, and more desirably from about 50% to about 70% by weight of the composition, and may, in the absence of other cosmetic adjuncts, form the balance of the composition.

Emollients are moisturizers to maintain hydration or to rehydrate the skin by providing a protective emollient coating. Emollients may be classified under such general chemical categories as esters, fatty acids and alcohols, polyols and hydrocarbons. Esters may be mono- or di-esters. Representative examples of fatty di-esters include, but are not limited to, dipotassium glycyrrhizinate, dibutyl adipate, diethyl sebacate, diisopropyl dimerate, and dioctyl succinate. Acceptable branched chain fatty esters include, but are not limited to, 2-ethyl-hexyl myristate, isopropyl stearate and isostearyl palmitate. Acceptable tribasic acid esters include, but are not limited to, triisopropyl trilinoleate and trilauryl citrate. Acceptable straight chain fatty esters include, but are not limited to, lauryl palmitate, myristyl lactate, and stearyl oleate.

Suitable fatty alcohols and acids may include, but are not limited to, alcohols or acids having from about 10 to 20 carbon atoms. For example, alcohols such as cetyl, myristyl, palmitic and stearyl alcohols and acids may be used.

Polyols may serve as emollients, including, but not limited to linear and branched chain alkyl polyhydroxyl compounds. Representative polyols, include, but are not limited to butylene, propylene glycol, sorbitol, glycerin, polymeric polyols, such as polypropylene glycol and polyethylene glycol, and the like.

Hydrocarbons may serve as emollients and may include hydrocarbon chains having from about 12 to 30 carbon atoms, including, but not limited to mineral oil, petroleum jelly, squalene and isoparaffins.

Exemplary emollients include, but are not limited to, butylene, caprylic/capric triglyerides, castor oil, ceteareth-20, ceteareth-30, cetearyl alcohol, ceteth 20, cetostearyl alcohol, cetyl alcohol, cetyl stearyl alcohol, cholesterol, cocoa butter, diisopropyl adipate, glycerin, glyceryl monooleate, glyceryl monostearate, glyceryl stearate, isoparaffins, isopropyl myristate, isopropyl palmitate, lanolin, lanolin alcohol, hydrogenated lanolin, isoparaffins, liquid paraffins, linoleic acid, mineral oil, oleic acid, petroleum jelly, phospholipids, polyethylene glycol, polyethylene glycol-7 glyceryl cocoate, polyethylene glycol-18 methyl ester dimethyl silane, polyoxyethylene glycol fatty alcohol ethers, polyoxypropylene 15-stearyl ether, polypropylene glycol propylene glycol, propylene glycol stearate, sorbitol, sphingolipids, squalene, steareth-2 or -100, stearic acid, stearyl alcohol, urea, white petrolatum, and the like.

Emollients may be present individually or collectively in an amount ranging from about 0.005% to 20% by weight of the total composition, desirably from about 0.1 wt % to about 10 wt %, more desirably from about 1.0 wt % to about 5.0 wt %.

Humectants are moisturizers that can bind water and retain it on the skin surface. Exemplary humectants include, but are not limited to, acetyl glucosamine, bisaccharide gum, butylene glycol, ethoxydiglycol, ethylene glycolpolypropylene, glucose, glycereth-26, glycerin, glycerol, glycol, lactitol, maltitol, propylene glycol, sericin, sodium hyaluronate, sorbitol, xylitol, sodium citrate, glucose and the like.

Humectants may be collectively present in an amount ranging from about 0.1% to 40% by weight of the total composition, desirably from about 2.5 wt % to about wt 25%, more desirably from about 5 wt % to about 15 wt %.

The present compositions may provide one or more preservatives. Suitable preservatives include disodium EDTA, benzyl alcohol, methylparaben, phenoxyethanol, propylparaben, ethylparaben, butylparaben and isobutylparaben.

Another category of functional ingredients within the cosmetic compositions of the present invention are thickeners. Thickeners will usually be present in a collective amount ranging anywhere from about 0.01 to 10% by weight, desirably from about 0.05 to 5% by weight, more desirably from about 0.1% to 1% by weight of the composition. Exemplary thickeners are cross-linked polyacrylate materials. Gums such as xanthan, carrageenan, gelatin, karaya, pectin and locust bean gum may be used. Under certain circumstances the thickening function may be accomplished by a material also serving as a silicone or emollient. For instance, silicone gums in excess of 10 centistokes and esters such as glycerol stearate have dual functionality.

In certain embodiments skin whitening agents may be included in the compositions of the present invention. Skin whitening agents include but are not limited to tyrosinase inhibitors, free radical scavengers, and mixtures thereof.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The compositions of the present invention may be formulated in any convenient form suitable for topical application to the skin. Such product forms include, but are not limited to, aerosol spray, cream, dispersion, emulsion, foam, gel, liquid, lotion, mousse, ointment, patch, pomade, pack or powder, pump spray, solid, solution, stick, and towelette. A desired cosmetic form is a cream that is an oil-in-water emulsion. Water-in-oil and water-in-silicone emulsions also are contemplated. In each formulation, various known conventional cosmetic ingredients may be incorporated. For example, cosmetic ingredients such as alcohols, fats and oils, surfactants, fatty acids, silicone oils, humectants, moisturizers, viscosity modifiers, emulsifiers, stabilizers, coloring agents, and perfumes may be included. The compositions may be administered as needed, daily, several times per day or in any suitable regimen such that the desired outcome is achieved. The compositions may be administered on a continuous basis or intermittent basis.

Certain embodiments relate to a cosmetic treatment system including a patch impregnated with the topical composition of the present invention. Patches for use in the present invention may come in any shape suitable for treating a particular target area. The patch may encompass a small area targeting a particular area or it may cover a large area, such as a face in the form of a mask. The overall size and geometry of current patches for applying medicaments around the eyes can make it difficult to apply eye treatment products in close proximity to the eye.

FIG. 1 depicts a representative patch 1 of the present invention. The patch includes a front side 3 and a back side 7 impregnated with the topical composition 5. When treating the eye area, the patch 1 may be kidney-shaped with convex ends, a smaller radiused first end 9, and a larger radiused second end 11 opposite the first end 9 with a top portion 10 having a surface that is substantially parallel to the curvature of the cheekbone adjacent to a subject's eye. The relatively shorter, more radiused design of the eye patch 1 depicted in FIG. 1 makes it easier for a subject 13 to position the patch 1 in close proximity to the eye 15, both under the eye 17 and near the side of the eye 19. However, for treatment of the area around the eye, the length, width, and geometry of the patch 1 set forth in e.g., FIG. 1 may be varied without negatively impacting its effectiveness. Moreover, the present invention may include a pair of patches 1 for treating each eye 15 individually, or it may contain a single, continuous patch for treating both eyes at once. A patch 1 for use with the present invention may be further adapted, fitted and/or cut in accordance to the particular contours or shape of the area to be treated. A skilled artisan will of course recognize that the front side 5 or the back side 7 of patch 1 may be impregnated with the topical composition 5, depending on the orientation of the patch 1 or the particular eye that is being treated.

The patch 1 may be made of any removal material suitable for absorbing, containing, and releasing compositions of the present invention. For example, the patch 1 may be made of non-woven material. The non-woven material may include cotton, cotton/polyester blends, or other suitable combinations of natural or synthetic materials. The patch may be further adapted to provide an occlusive, semi-occlusive or non-occlusive barrier. The patch may be adhesive or non-adhesive. As depicted in FIG. 1, the patch 1 may include a single layer of material 21 or it may include multiple layers of the same and/or dissimilar materials to provide additional structural integrity and/or flexibility. Suitable patches or patch materials are disclosed in e.g., U.S. Pat. Nos. 6,096,334; 6,120,792; 6,495,158; 6,623,751; 8,697,099; U.S. Pat. Appl. No. 2002/0086043; U.S. Pat. Appl. No. 2003/0152610; U.S. 2003/0175328; and references cited therein, the contents of which are incorporated herein by reference.

The topical composition 5 may be coated onto at least a portion of the patch 1 immediately prior to applying the patch 1 to a subject 13. Alternatively, the patch 1 may be pre-coated with the topical composition and ready for use. Preferably, the topical composition 5 is applied to substantially the entire surface back 7 of the patch 1. The patch 1 and/or the topical composition 5 may further include an adhesive 23. The adhesive 23 may be applied to the back 7 of the patch 1 prior to or subsequent to applying the topical composition 5 to the patch 1. The adhesive 23 may be any adhesive known to those skilled in the art and suitable for removably adhering the patch and/or topical composition to a substrate, such as human skin. The adhesive may be applied to the front side 5 or the back side 7 of patch 1, depending on the orientation of the patch 1 or the particular side impregnated with the topical composition.

The cosmetic treatment system of the present invention may include a packaging system for holding the individual components of the cosmetic treatment system. In a preferred embodiment, the cosmetic treatment system includes a patch; at least one container; and a topical composition formulated for treatment of an area in close proximity to the eye.

Figure 3:
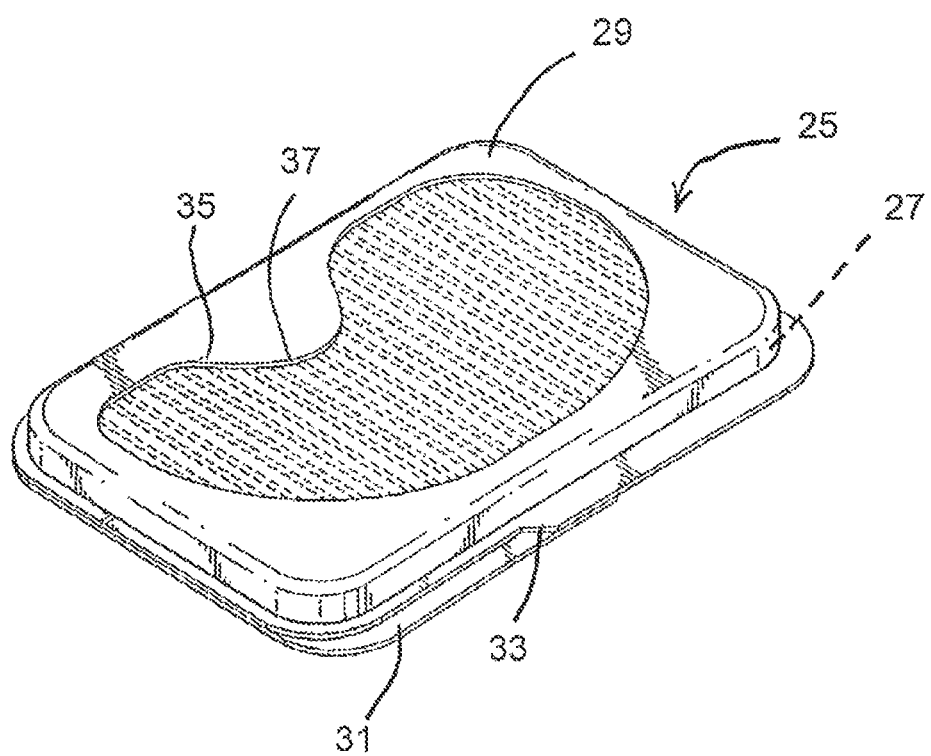
FIG. 3 shows a representative container for holding the patch of FIG. 1.

One or more containers may be used to hold one or more of the components of the cosmetic treatment system. Any container(s) suitable for holding the components of the cosmetic treatment system may be used in accordance with conventional practices known to those skilled in the art. FIG. 3 depicts a representative container 25 adapted for holding the patch 1. The rectangular container 25 includes an interior 27, a top cover 29 and a base portion 31. The top cover 29 may include an indent 33 for opening or separating the top cover 29 from the base portion 31, to facilitate retrieval of the patch 1 held in place by a sunken cavity having a sufficient depth 35 and shape 37 complementarily adapted for securely holding the patch 1 of FIG. 1 in the base portion 31. Alternatively, the patch may be packaged in a container in the form of a sunken tray overlayed with a sealably removable cover to securely maintain the patch in the sunken tray prior to use.

Figure 2:
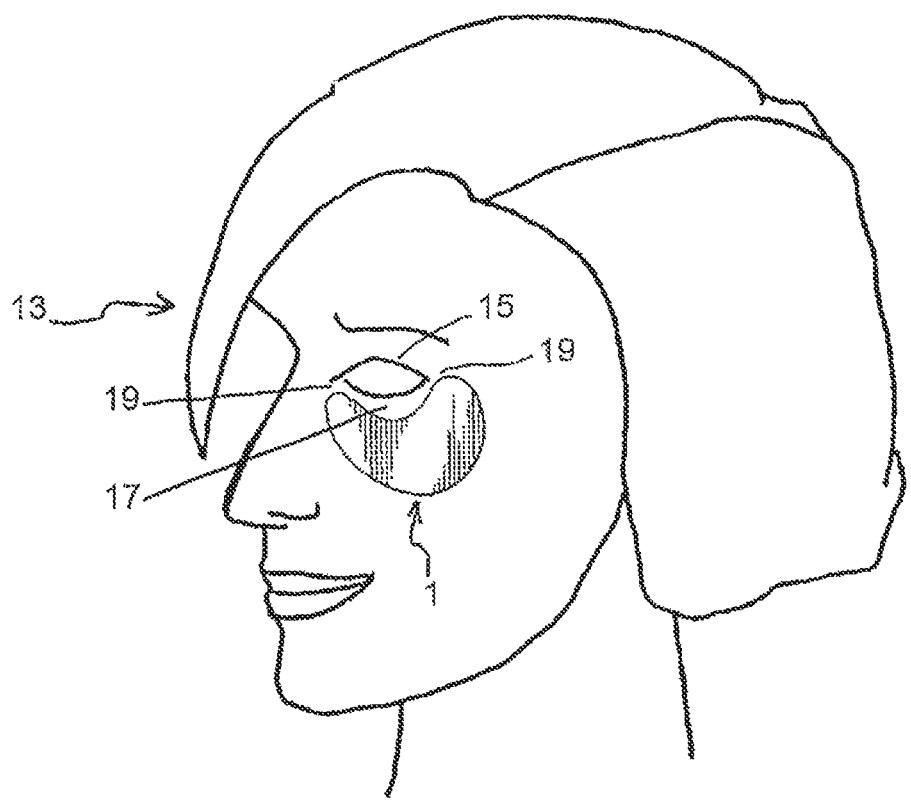
FIG. 2 shows the patch of FIG. 1 affixed to a portion of a subject's face under the subject's left eye.

The container may be prepared by thermoforming or by thin-wall injection molding of a suitable material, such as polypropylene. The design of the container 25 can be modified and adapted to the shape of the particular patch. The container 25 may be formulated for holding only the patch or it may be formulated to hold the patch 1, as well as the other components of the cosmetic treatment system, including the topical composition 5 and/or an adhesive 23 for promoting the adherence of the topical composition 5 and/or patch 1 to a subject 13 as exemplified in FIG. 2. Suitable containers for holding patches of the present invention are disclosed in U.S. Pat. No. 6,623,751, the contents of which are incorporated herein by reference.

Certain embodiments relate to topical composition(s) that may be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. In certain embodiments, a closed container containing a cosmetically acceptable composition as herein defined may be used.

Certain further embodiments relate to a cosmetic treatment system including a packaging system containing a suitable amount of the cosmetic composition suitable for a desired period of time, such as fourteen days. According to this embodiment, the cosmetic treatment system includes a packaging system containing a plurality of containers, with each container having an amount of the cosmetic composition according to the present invention suitable for a single use. The container may be in the form of a vial or other suitable holding device.

In one embodiment, the cosmetic treatment system includes a packaging system having a plurality of vials, each vial containing a sufficient amount of the cosmetic composition suitable for a single application of the cosmetic composition to the skin. The packaging system may be formulated to provide a number of vials matching the number of days in which the cosmetic composition is applied to skin. Alternatively, the packaging system may be formulated for more than one application per day. In one embodiment, the packaging system may contain 14 vials for daily treatment to skin over a period of 14 days. The packaging system may further contain one or more applicators for applying the compositions and may further include a set of instructions for use of the packaging system associated with the cosmetic treatment system.

The present invention also includes methods of treating skin by topically applying the cosmetic compositions of the present invention. In use, a small quantity of the composition, for example from 0.1 to 100 mL, may be applied to exposed areas of the skin, from a suitable container or applicator and, if necessary, it is then spread over and/or rubbed into the skin using the hand or fingers or a suitable device. Alternatively, the composition may be applied to the skin in the form of a patch that has been impregnated with the composition. The patch may be made of non-woven material and may further contain an adhesive to adhere the patch to the skin.

Certain embodiments relate to a method for preventing, arresting, reversing, ameliorating, diminishing, reducing or improving a sign of aging, in which a composition of the present invention is topically applied to skin in a cosmetically effective amount sufficient to prevent, arrest, reverse ameliorate, diminish, reduce or improve a sign of aging in skin. Exemplary signs of aging include, but are not limited to, facial lines, fine lines, wrinkles, crow's feet, dark eye circles, blemishes, age spots, stretch marks, or combinations thereof.

Certain other embodiments relate to a method for improving the aesthetic appearance of skin, in which a composition of the present invention is topically applied to skin in a cosmetically effective amount sufficient to improve the aesthetic appearance of the skin. The improvements may relate to skin thickness, elasticity, resiliency, moisturization, tone, texture, radiance, luster, lightening, brightness, clarity, contour, firmness, tautness, suppleness, softness, sensitivity, pore size, or combinations thereof.

The improvements may further relate to improving adverse skin conditions affected by, resulting in or resulting from the group consisting of psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The signs of aging or adverse skin conditions may result from free radical damage, environmental agents, pollutants, diet, chronological aging, premature aging, hormonal aging, photo-aging, or combinations thereof. Accordingly, the present compositions and methods selected for improved anti-aging characteristics or adverse skin conditions may employ topical application of active ingredients inhibiting enzymes or mediators that accelerate or facilitate aging, damage, formation of free radicals, or breakdown of skin elements, including, but not limited to metalloproteinases, collagenases, elastases, hyaluronidases, and proteases. The active ingredients may have anti-oxidant activity, free radical scavenging or anti-inflammatory activity and/or they may inhibit breakdown of collagen, elastin, fibronectin, hyaluronic acid, glycosaminoglycans (GAG) or other extracellular matrix elements or regulatory enzymes or mediators of the NF-kB signal transduction pathway. The active agents may also inhibit other signal transduction pathways associated with aging, including the mediators and regulators associated with these pathways, or combinations thereof.

The active agent(s) may also modulate an inducible nitric oxide synthase (iNOS) protein expression in a skin, activate peroxisome proliferator activator receptor gamma (PPARγ) (and thus regulate fatty acid storage glucose metabolism) in skin cells, decrease a skin anti-inflammatory response, increasing superoxide dismutase activity in a skin, increase anti-oxidant response elements (ARE), and stimulating or increasing matrix metalloproteinase activity.

Certain embodiments relate to a method of modulating iNOS protein expression in a skin cell comprising applying to a skin of a subject a composition in a cosmetically effective amount sufficient to modulate iNOS protein expression the skin, wherein the composition comprises an amount of sesamin, individually or in combination with at least one other plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof, and at least one pharmaceutically or cosmetically acceptable vehicle. The nitric oxide synthases (NOS) are central to the production of the highly reactive nitric oxide (NO) and the various species produced by its oxidation or reduction (for example $NO_2$, $N_2O_3$, $N_2O_4$). Of the three NOS isoforms, nNOS/NOS1 and eNOS/NOS3 (neuronal and endothelial NOS) are dependent on intracellular calcium levels and in general are constitutively expressed, whilst iNOS (or NOS2) is calcium-independent and rapidly induced in response to inflammation and infection. In addition to their role in the innate immune response iNOS and NO have been implicated in a wide spectrum of human physiological responses and diseases including but not limited to autoimmune reactions, tumor growth, and diabetes. Furthermore, keratinocytes, which make up the bulk of the epidermis, constitutively express the neuronal isoform of NO synthase (NOS1), whereas the fibroblasts in the dermis and other cell types in the skin express the endothelial isoform (NOS3). Under certain conditions, virtually all skin cells appear to be capable of expressing the inducible NOS isoform (NOS2) (*Nitric Oxide*, (4):179-93 (2004)). Use of compositions that are capable of modulating iNOS in the skin may result in improvement of the appearance of skin or at least one sign of aging in skin.

Further embodiments relate to a method of activating peroxisome proliferator activator receptor gamma (PPARγ) (and thus regulating fatty acid storage glucose metabolism) in skin cells comprising applying to a skin a composition in a cosmetically effective amount sufficient to activate PPARγ in the skin, wherein the composition comprises an amount of sesamin, individually or in combination with at least one other plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof and at least one pharmaceutically or cosmetically acceptable vehicle. PPARγ is a ligand-dependent transcription factor and a member of the nuclear receptor superfamily. Acting as sensors of hormones, vitamins, endogenous metabolites and xenobiotic compounds, the nuclear receptors control the expression of a very large number of genes. More recently, PPARγ has been recognized as playing a fundamentally important role in the immune response through its ability to inhibit the expression of inflammatory cytokines and to direct the differentiation of immune cells towards anti-inflammatory phenotypes (*Mutat Res.*, 690(1-2):57-63 (2010)). Use of compositions that are capable of activating PPARγ in the skin may result in improvement of the appearance of skin or at least one sign of aging in skin.

Yet other embodiments relate to a method of decreasing a skin anti-inflammatory response comprising applying to the skin a composition in a cosmetically effective amount sufficient to decrease the skin anti-inflammatory response, wherein the composition comprises an amount of sesamin, individually or in combination with at least one other plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof, and at least one pharmaceutically or cosmetically acceptable vehicle. The activation of anti-oxidant pathways was measured by creating stable monoclonal HepG2 cells containing a luciferase gene under the control of antioxidant response elements. Use of compositions that are capable of decreasing a skin anti-inflammatory response in the skin may result in improvement of the appearance of skin or at least one sign of aging in skin.

Another embodiment relates to a method of increasing superoxide dismutase (SOD) activity in a skin cell comprising applying to the skin a composition in a cosmetically effective amount sufficient to increase superoxide dismutase activity in the skin, wherein the composition comprises an amount of sesamin, individually or in combination with at least one other plant ingredient or plant extract from *Pistacia* (e.g., *Pistacia lentiscus*), *Leontopodium* (e.g., *Leontopodium alpinium*), *Spirulina* (e.g., *Spirulina platensis*), *Oroxylum* (e.g., *Oroxylum indicum*), *Schizandra* (e.g., *Schizandra chinesis*), *Moringa* (e.g., *Moringa pterygosperma*), *Houttuynia* (e.g., *Houttuynia cordata*), *Isodon* (e.g., *Isodon japonicus*), and *Saxifraga* (e.g., *Saxifraga stolonifera*), or mixtures thereof, and at least one pharmaceutically or cosmetically acceptable vehicle. SOD is an enzyme that alternately catalyzes the dismutation (or partitioning) of the toxic superoxide ($O_2^-$) radical into either ordinary molecular oxygen ($O_2$) or hydrogen peroxide ($H_2O_2$). Superoxide is produced as a by-product of oxygen metabolism and causes many types of cell damage. Hydrogen peroxide is also damaging, but less so, and is degraded by other enzymes such as catalase. Thus, SOD is an important antioxidant defense in nearly all living cells exposed to oxygen and may be important in skin anti-aging (e.g., improvement of the appearance of skin or at least one sign of aging in skin). Use of compositions that are capable of increasing SOD in the skin may result in improvement of the appearance of skin or at least one sign of aging in skin.

A further embodiment relates to a method of stimulating or increasing matrix metalloproteinase (MMP) activity in a skin cell comprising applying to the skin a composition in a cosmetically effective amount sufficient to stimulate or increase matrix metalloproteinase activity in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, and at least one pharmaceutically or cosmetically acceptable vehicle. MMPs are zinc-dependent endopeptidases. The MMPs belong to a larger family of proteases known as the metzincin superfamily. Collectively, these enzymes are capable of degrading all kinds of extracellular matrix proteins, but also can process a number of bioactive molecules. They are known to be involved in the cleavage of cell surface receptors, the release of apoptotic ligands (such as the FAS ligand), and chemokine/cytokine inactivation. MMPs are also thought to play a major role on cell behaviors such as cell proliferation, migration (adhesion/dispersion), differentiation, angiogenesis, apoptosis, and host defense. Stimulating or increasing matrix metalloproteinase activity in a skin may result in improvement of the appearance of skin or at least one sign of aging in skin. Use of compositions that are capable of stimulating or increasing MMP activity in the skin may result in improvement of the appearance of skin or at least one sign of aging in skin.

Figure 4:
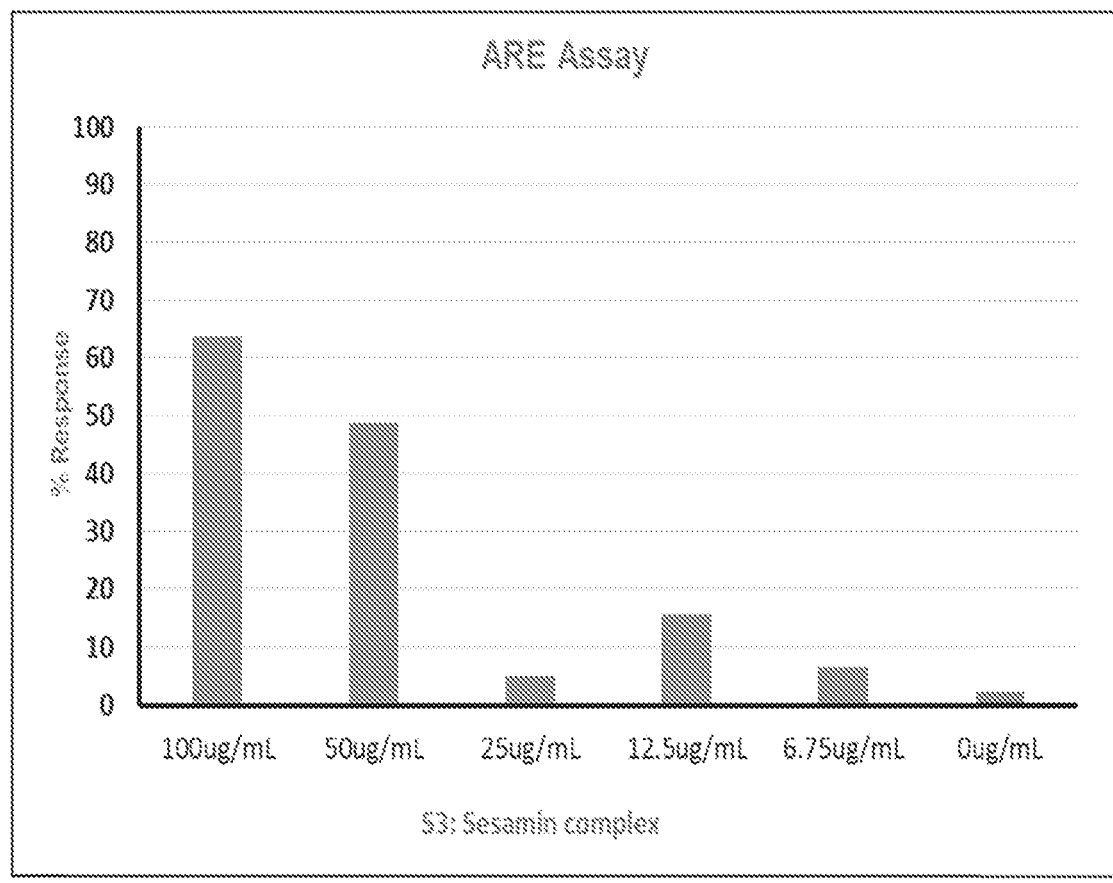
FIG. 4 depicts a graph of anti-oxidant response elements (ARE).

Another embodiment relates to a method of increasing ARE response in a skin cell comprising applying to the skin a composition in a cosmetically effective amount sufficient to increase ARE response in the skin, wherein the composition comprises an amount of sesamin, individually or in combination with at least one plant ingredient or plant extract from *Pistacia, Leontopodium, Spirulina, Oroxylum, Schizandra, Moringa, Houttuynia, Isodon*, and *Saxifraga*, or mixtures thereof, and at least one pharmaceutically or cosmetically acceptable vehicle. Antioxidant responsive elements (AREs) mediate the transcriptional induction of a battery of genes which comprise much of this chemoprotective response system. AREs mediate the transcriptional induction of a battery of genes, which comprise much of this chemoprotective response system. Past studies identified a necessary ARE "core" sequence of RTGACnnnGC (SEQ ID NO:1), but this sequence alone is insufficient to mediate induction. Herein, the additional sequences necessary to define a sufficient, functional ARE are identified through systematic mutational analysis of the murine GST Ya ARE. Introduction of the newly identified necessary nucleotides into the regions flanking a nonresponsive, ARE-like, GST-Mu promoter sequence produced an inducible element. A screen of the GenBank database with the newly identified ARE consensus identified 16 genes, which contained the functional ARE consensus sequence in their promoters. Included within this group was an ARE sequence from the murine ferritin-L promoter that mediated induction when tested. As shown in FIG. 4, a dose-dependent anti-oxidant response was observed with treatment sesamin complex suggesting activation of anti-oxidant pathways. A control sample without sesamin complex showed no response.

In addition to improving the aesthetic or cosmetic appearance of skin, the topical compositions of the present invention may be topically applied to enhance the general health, vitality and appearance of the skin. For example, the present composition may be applied to skin to improve microcirculation, communication among skin cells, replenishment of essential nutrients or skin constituents, or to improve the metabolism, proliferation, multiplication, turnover and/or exfoliation of skin cells.

Exfoliation may be carried out with or without the use of alpha- or beta hydroxy acids or other exfoliants, or combinations thereof by topical application to skin. When using exfoliating agents in the compositions of the present invention, sufficient anti-irritant or anti-inflammatory agents are included to neutralize the potential irritation associated with exfoliating agents in the absence of such neutralizing agents.

In certain embodiments, the compositions described herein may be used for various cosmetic and/or pharmaceutical applications including skin whitening and lightening.

Certain embodiments relate to a method of whitening skin that includes topically applying to the skin any composition described above and any combinations thereof.

The following are non-limiting examples of the present invention. Unless indicated otherwise, all proportions and percentages are by weight.

EXAMPLES

The following are examples of formulations according to the present invention.

Sample Preparation:

Unless otherwise stated, sesamin complex was prepared in 70% DMSO (Dimethyl sulfoxide) and diluted to their respective concentrations identified in the respective figure legends. The final DMSO concentrations were maintained at 0.05% or lower.

Example 1

Anti-Oxidant Response Element Assay

Sesamin complex was dissolved in 70% DMSO and finally diluted 1:15 in MEM containing Myrosinase (0.625 U/mL) and Ascorbic Acid (350 uM) and the final concentration of DMSO was 0.14%.

The activation of anti-oxidant pathways was measured by creating stable monoclonal HepG2 cells containing a luciferase gene under the control of antioxidant response elements. The cells were grown in minimum essential media (MEM) with 10% fetal bovine serum and 150 ug/mL of hygromycin in a humidified atmosphere containing 5% CO2 at 37 C. For the assay, the cells were seeded at a density of 31,250 cells per well in a 96-well, white-walled, collagen coated plate. The following day, the media was removed and fresh growth media was added. After 24 hours, the cells were treated with test compounds for 48 hours (100 ug/mL, 50 ug/mL, 25 ug/mL, 12.5 ug/mL, and 6.75 ug/mL), lysed and the amount of luciferase produced was measured using a luciferase activity assay. Data were captured as relative luminescence units (RLUs) using an M5 Spectrophotometer (Molecular Devices, Inc). These data were normalized to background RLUs in untreated (0%) and positive control (Sulforophane-treated; 100%) wells and presented as "% Response."

Final concentration levels of sesamin in the study are presented in FIG. 4. As shown in FIG. 4, the highest anti-oxidant response was observed with treatment with 100 ug/mL sesamin complex, followed by treatment with 50 ug/mL sesamin suggesting activation of anti-oxidant pathways at these concentrations. A control sample without sesamin complex showed no response.

Example 2

Melanin Inhibition Assay

Melan-a cells seeded at a density of $5 \times 10^4$ cells per well were grown in a 24 well plate. Sesamin complex (S1) (at the concentrations indicated in the legend of FIG. 5) was dissolved in (DMSO) such that the final concentration of DMSO in the culture medium was maintained at 0.05%. Sesamin complex and Phenylthiourea (PTU) was added to the cells in triplicate and incubated for 2 days following which the cells were again treated with compounds supplemented with fresh medium. PTU at a concentration of 60 ug/ml was used as a positive inhibitor control in the melanin inhibition assay. Two days later, melanin was extracted and quantitated by normalizing with the protein content. After 4 days, melanin was extracted and cleared of the cell debris from each of the wells were dissolved by treating with 2N NaOH in 20% DMSO and incubating the samples for 60 min at 55° C. The melanin content in each sample was determined by measuring absorbance at 490 nm. Data were presented as % melanin content normalized to protein content in untreated wells compared to % melanin content extracted from samples.

Figure 5:
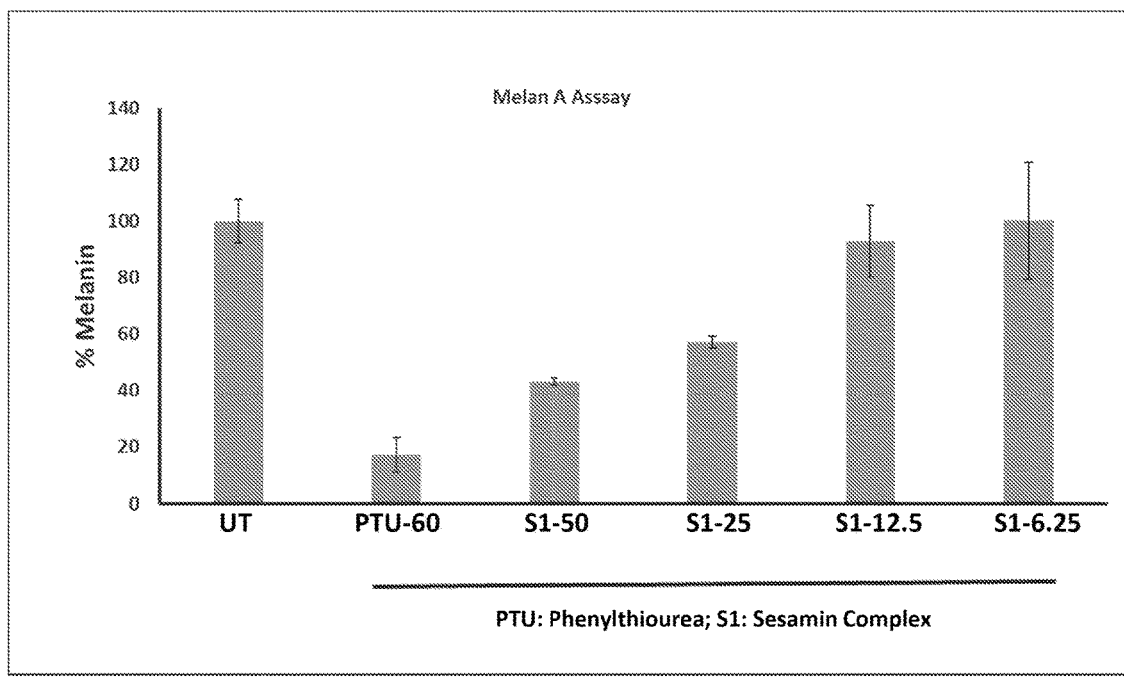
FIG. 5 depicts a graph of skin lightening activity of sesamin in a melanin A assay.

As shown in FIG. 5, a dose dependent melanin inhibition was observed in cells treated with sesamin complex.

Example 3

Sesamin Activation: Peroxisome Proliferator Activator Receptor Gamma (PPARγ) Activation Assay (Sesamin Testing)

Reagents:

Troglitazone (positive control) was purchased from Sigma Corp. Sesamin sample was purchased from Virun Chemicals and a stock solution at a concentration of 100 mg/mL was prepared in 70% Dimethyl Sulfoxide (DMSO) and diluted to the indicated concentrations as shown in the figure. The final concentration of DMSO was maintained at 0.05% or lower.

Sample Preparation:

Stock solutions of troglitzone and sesamin samples were solubilized and diluted in DMSO prior to dilution in Dubelco's minimum essential media (DMEM) containing 0.5% Bovine serum Albumin (BSA) for testing.

Gal4-PPAR Ligand Binding Domain (LBD) Constructs:

To study the activation of PPARγ in a luciferase reporter assay, a Gal4-PPARγ-ligand-binding domain (LBD) vector was created in a modified pFN26A (BIND) vector (Promega Inc). The PPARγ-LBD (residues 203-477) was PCR amplified from human MGC: 5041 (pSPORT6; Open Biosystems Inc.) and ligated into the pBIND3 vector forming a Gal4-PPARγ-LBD fusion protein.

PPARγ Reporter Cell Line Development:

Dual vector stable cell lines for PPARγ LBD assays were generated by first transfecting CHO-K1 cells with pGL4.35 [luc2P/9XGAL4 UAS/Hygro] vector according to the manufacturer's instructions for Fugene 6 (Promega Inc.). Hygromycin (300 μg/mL) supplemented media was used to screen for monoclonal cell lines 24 hours after transfection, and selected monoclonal cell lines were screened by dilution method until there was no further cell death. The PPARγ containing cell lines were then created by transfecting the stable pGL4.35 9XUAS Luc2P CHO-K1 cell line with the pBIND3 Gal4-PPARγ-LBD vector and selecting pBIND3 Gal4-PPARγ-LBD containing cells with 600 μg/mL of G418. The resulting stable cells lines were maintained with growth media supplemented with 150 μg/mL hygromycin and 300 μg/mL G418.

PPARγ Reporter Assays.

To test for activation of the PPARγ, ~15,000 dual transfected cells were plated per well in white walled 96 well plates. After 24 hours, the media was changed to F12K media lacking FBS but containing 0.5% BSA and incubated for another 24 hours. Test compounds (troglitazone and sesamin samples) were diluted in DMEM containing 0.5% BSA to a final constant concentration of 0.1% DMSO and added to the cells then incubated 18-24 hours. Luciferase was quantified using an activity assay from Biotium Inc. Briefly, at time of analysis, cells in white-walled 96-well plates were rinsed once using 50 μL of DPBS, then lysed with 20 μL of 1× passive lysis buffer. Lysis proceeded for ~20 min at room temperature. Reconstituted, room temperature D-luciferin was added (100 μL per well) and light emission was immediately read using an M-5 spectrophotometer (Molecular Devices, Inc.).

Figure 6:
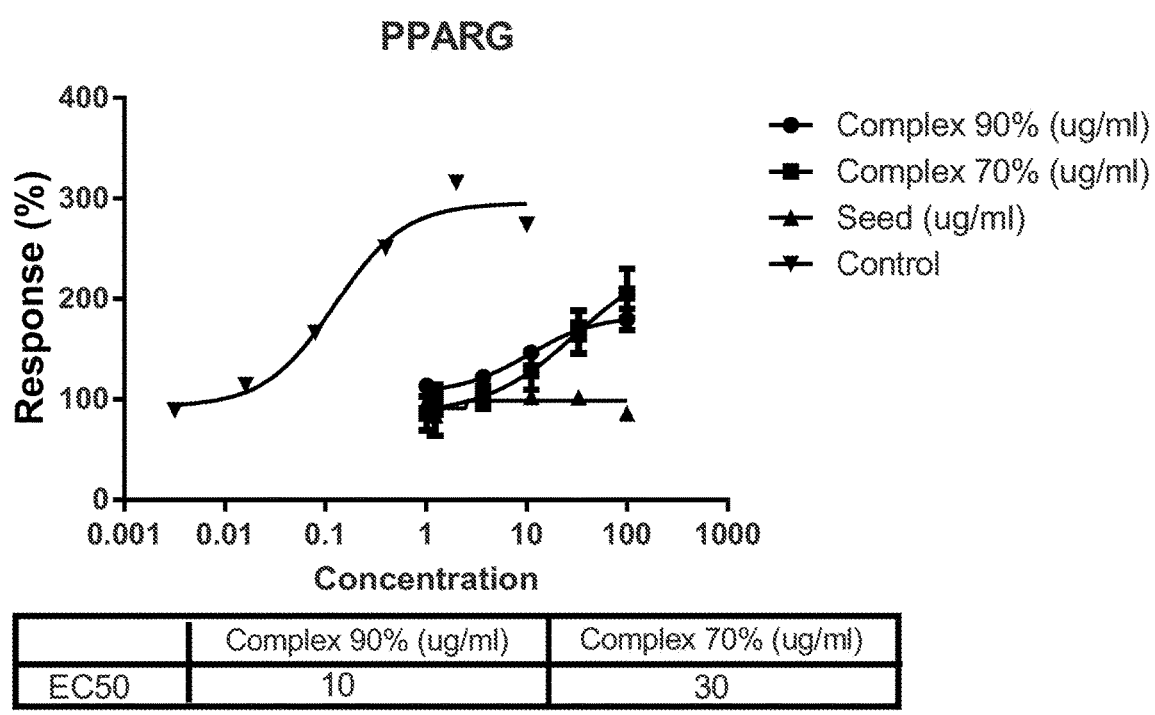
FIG. 6 depicts a graph of PPARγ response of sesamin.

The results for the activation of the PPARγ are shown in FIG. 6. Data points presented are in final concentrations versus percent of control response, mean±SD, n=2. As shown in FIG. 6, sesamin at 90% (μg/mL) and 70% (μg/mL) showed a dose-dependent activation of PPARγ. The data suggest that sesamin may regulate fatty acid storage glucose metabolism and may be useful in combating skin aging problems. Also, the data suggest that sesamin may cause a decrease in inflammatory response of cells.

It is therefore intended that the foregoing detailed description be regarded as illustrative rather than limiting, and that it be understood that it is the following claims, including all equivalents, that are intended to define the spirit and scope of this invention.

The invention claimed is:

1. A topical composition comprising:
   a. an amount of a hydro-ethanolic extract of *Sesamum* comprising sesamin and effective to improve the appearance of skin or at least one sign of aging in skin;
   b. at least two plant ingredients or plant extracts from *Pistacia, Leontopodium, Spirulina, Oroxylum, Moringa, Houttuynia, Isodon*, and *Saxifraga*, or mixtures thereof; and
   c. at least one pharmaceutically or cosmetically acceptable vehicle,
   wherein the composition is in a product form selected from the group consisting of an aerosol, a cream, an emulsion, a solid, a liquid, a dispersion, a foam, a gel, a lotion, a mousse, an ointment, a powder, a patch, a pomade, a solution, a pump, a spray, a stick, a towelette, and combinations thereof.

2. The topical composition of claim 1, further comprising at least one DNA repair enzyme.

3. The topical composition of claim 2, where the at least one DNA repair enzyme is a pyrimidine glycosylate/abasic lyase.

4. The topical composition of claim 2, where the at least one DNA repair enzyme is selected from the group consisting of a bacteriophage T4 pyrimidine dimer-specific endonuclease, a *Micrococcus luteus* N-glycosylase/AP lyase, a *Saccharomyces cerevisiae* N-glycosylase/apurinic-apyrimidinic lyase, a *Schizosaccharomyces pombe* UV damage endonuclease (UVDE), a *Chlorella* virus isolate PBCV-1 pyrimidine dimer-specific glycosylase, an *Anacystis nidulans* photolyase, and combinations thereof.

5. The topical composition of claim 1, where the at least one pharmaceutically or cosmetically acceptable vehicle includes one or more ingredients selected from the group consisting of water, a glycerin, a C1-C4 alcohol, a fatty alcohol, a fatty ether, a fatty ester, a polyol, a glycol, a vegetable oil, a mineral oil, a liposome, a laminar lipid material, a silicone oil, and combinations thereof.

6. The topical composition of claim 1, wherein the composition has a neutral pH.

7. The topical composition of claim 1, further comprising a skin whitening agent selected from the group consisting of tyrosinase inhibitors, free radical scavengers, and mixtures thereof.

8. The topical composition of claim 1, wherein the amount of the hydro-ethanolic extract of *Sesamum* comprising sesamin, individually or in combination with at least two plant ingredients or plant extracts from *Pistacia, Leontopodium, Spirulina, Oroxylum, Moringa, Houttuynia, Isodon*, and *Saxifraga*, or mixtures thereof, effective to improve the appearance of skin or at least one sign of aging in skin ranges from about 0.0001% to 5% by weight of the total composition.

9. The topical composition of claim 1, wherein the amount of the hydro-ethanolic extract of *Sesamum* comprising sesamin, individually or in combination with at least two plant ingredients or plant extracts from *Pistacia, Leontopodium, Spirulina, Oroxylum, Moringa, Houttuynia, Isodon*, and *Saxifraga*, or mixtures thereof, effective to improve the appearance of skin or at least one sign of aging in skin ranges from about 0.001% to about 0.5% by weight of the total composition.

10. The topical composition of claim 1, wherein the amount of the hydro-ethanolic extract of *Sesamum* comprising sesamin, individually or in combination with at least two plant ingredients or plant extracts from *Pistacia, Leontopodium, Spirulina, Oroxylum, Moringa, Houttuynia, Isodon*, and *Saxifraga*, or mixtures thereof effective to improve the appearance of skin or at least one sign of aging in skin ranges from about 0.01% to about 0.1% by weight of the total composition.

11. A packaging system for improving the appearance of skin or at least one sign of aging in skin comprising:
a. one or more containers collectively containing the composition of claim1; and
b. instructions for applying the composition from said one or more containers.

12. A topical composition comprising:
a. an amount of a hydro-ethanolic extract of *Sesamum* comprising sesamin and effective to improve the appearance of skin or at least one sign of aging in skin;
b. at least three plant ingredients or plant extracts from *Pistacia, Leontopodium, Spirulina, Oroxylum, Moringa, Schizandra, Houttuynia, Isodon*, and *Saxifraga*, or mixtures thereof; and
c. at least one pharmaceutically or cosmetically acceptable vehicle,
wherein the composition is in a product form selected from the group consisting of an aerosol, a cream, a emulsion, a solid, a liquid, a dispersion, a foam, a gel, a lotion, a mousse, an ointment, a powder, a patch, a pomade, a solution, a pump, a spray, a stick, a towelette, and combinations thereof.

* * * * *